United States Patent
Horn

(10) Patent No.: US 6,383,413 B1
(45) Date of Patent: May 7, 2002

(54) PROCESS FOR THINNING OF PHOSPHINE WITH AIR WITHOUT DANGER OF BURNING

(76) Inventor: Pedro Miguel Horn, Marchant Pereira 367, 901 Providencia Santiago Chile (CL)

( * ) Notice: Subject to any disclaimer, the term of this patent is extended or adjusted under 35 U.S.C. 154(b) by 0 days.

(21) Appl. No.: 09/385,942

(22) Filed: Aug. 30, 1999

(30) Foreign Application Priority Data

Aug. 28, 1998 (DE) .......................................... 198 39 385

(51) Int. Cl.[7] .............................................. C01B 25/06
(52) U.S. Cl. ..................................... 252/372; 423/299
(58) Field of Search ......................... 423/299; 422/129; 252/372

(56) References Cited

U.S. PATENT DOCUMENTS

| | | | | |
|---|---|---|---|---|
| 3,371,994 A | * | 3/1968 | Lowe et al. ................. | 423/299 |
| 3,375,074 A | * | 3/1968 | Palmer ........................ | 423/299 |
| 3,583,909 A | * | 6/1971 | Block .......................... | 423/299 |
| 4,597,776 A | * | 7/1986 | Ullman et al. .............. | 423/659 |
| 4,814,154 A | * | 3/1989 | Doernemann et al. ...... | 423/299 |
| 5,098,664 A | * | 3/1992 | Schellhaas et al. ......... | 422/222 |
| 5,820,840 A | * | 10/1998 | Horn Feja et al. .......... | 423/299 |

FOREIGN PATENT DOCUMENTS

| | | | | |
|---|---|---|---|---|
| DE | 69129456 | | 12/1991 | ........... C01B/25/06 |
| EP | 536196 | * | 12/1991 | |
| WO | 9325075 | | 12/1993 | ........... A01N/25/18 |

* cited by examiner

Primary Examiner—Wayne Langel
(74) Attorney, Agent, or Firm—Horst M. Kasper

(57) ABSTRACT

A process and a device are provided for for thinning phosphine with air without a danger of burning. The process is carried out in this way that the mixing of phosphine and air is carried out under water or in the presence of water. The device consisting of a water-container which carries at least one introducer pipe for phosphine and at least one introducer pipe for air.

16 Claims, 4 Drawing Sheets

PROCESS FOR THINNING OF PHOSPHINE WITH AIR WITHOUT DANGER OF BURNING

BACKGROUND OF THE INVENTION

1. Field of the Invention

The present invention relates to the field of handling the gas phosphine without generating dangers.

2. Brief Description of the Background of the Invention Including Prior Art

Phoshine (=hydrogenphosphide, formula $PH_3$) is used since more than 50 years as pesticide and for pest-prophylaxis in the area of storage-protection, especially in the area of fodder and food.

Phosphine has some special properties which are of great importance for the modern pesticide-practice.

Thus, for example, phosphine is only very little soluble in water, oil and grease and will be nearly not absorbed by most of the food-materials. Phosphine is also not reacting with treated food with the consequence that the food carries no phosphine-residues after the treatment.

Due to the fact that phosphine is principally very little soluble and has a specific weight similar to air, phosphine can be distributed easily in big stores and storage containers.

When air will be put into contact with stores which have been treated by phosphine, the phosphine will be oxydized quickly to phosphorus-acid by UV-radiation with the consequence that no compounds will be created which contaminate the environment.

Further it is stated that in the last years it has been detected that phosphine is created spontaneously in the free nature.

On the other hand it has to be said that the above mentioned treatment with phosphine is accompanied by some problems. Phosphine present together with air results in a mixture which is easily flammable.

The limit of composition before ignition of this gas-mixture is 1.8% phosphine in air. If the concentration of phosphine surpasses this limit then the phosphine has an increased tendency of self-ignition.

On the other hand in the area of pesticides no high concentrations of phosphine are however necessary. An effective treatment will be achieved already by a phosphine-concentration of 200 to 300 ppm with the consequence that in the pesticide area there should not exist a danger of ignition. Nevertheless it cannot be excluded that under certain conditions sometimes higher phosphine-concentrations will arise with the consequence of self-ignition.

The experts in this field have presented a large number of proposals to solve this problem.

In order to use phosphine without danger it has been proposed for example to press paraffinated aluminiumphosphide (formula AlP) together with ammoniumcarbamate into tablets. These tablets will be exposed to the humidity of the air with the consequence that the AlP will be transformed to $PH_3$ and aluminum semi hydroxide AlOOH slowly by hydrolysis. The originated phosphine will be thinned down instantly by the surrounding air and thereby preventing ignition. Unfortunately the solid residue of this method has a content of 1–3% of AlP which has not reacted. Furthermore also magnesiumphosphid $Mg_3P_2$-compounds have been prepared and used in the pesticide-area, which will react with the humidity of air nearly totally with the consequence that the residues will have a very little content of poison.

The hydrolysis cannot be interrupted anymore after beginning of the reaction in all solid forms which are presented and which react with air-humidity to build phosphine. Furthermore the tablets must be dispersed in such a manner that no agglomerations will take place.

In present days it will be tried to use nitrogen-gas or $CO_2$ as thinning medium for phosphine in the gas-treatment field against pests. Hereby, it is absolutely necessary to use phosphine-gas, which is very much thinned in order not to exceed the ignition limit concentration of 1.8%. The gas will be transported in pipe-lines to the gas-treatment-objects. Thus it is possible to stop the supply of gas at any desired time and to add air as required to the subject composition. The disadvantage of this method is the fact that a great number of steel-cylinders, which contain thinned phosphine, must be transported, with the consequence that such methods work only with difficulty and are troublesome. Furthermore a generator has been created by which, beginning with $Mg_3P_2$, a mixture of air and phosphine will be produced. Unfortunately, also in using this generator, it cannot be excluded that under certain circumstances the ignition limit concentration will be exceeded with the consequence of self-ignition.

Therefore the problem is pure phosphine coming directly from the pressure-container with air up to under the ignition-limit and to use the produced gas-mixture against pests. By this method the transportation-cost is reduced considerably, and therefore the gas treatment is much cheaper.

Unfortunately, during the known thinning processes ignition cannot be excluded; in a case where a burning of phosphine has already started in the air, an extinguishing of such a flame can become very difficult. No process or method is known in the prior art by which it is possible to mix phosphine directly with air without a danger of ignition.

SUMMARY OF THE INVENTION

1. Purposes of the Invention

Ait is an object of the present invention to furnish a method for mixing phosphine directly with air without a danger of ignition.

These and other objects and advantages of the present invention will become evident from the description which follows.

2. Brief Description of the Invention

The present invention is based on the observation that phosphine, which has impurity-contents of Di- and Polyphosphine, has a higher tendency of self-ignition compared with pure phosphine, which has been produced from $Mg_3P_2$.

The present invention solves the problem to create a method and an apparatus which carry out a direct mixing of phosphine and air without any danger of ignition.

Surprisingly it has been found that by a mixing of phosphine and air under water the danger a self-ignition is eliminated. Hereby any relation phosphine/air can be held: When the phosphine will be thinned up to under the ignition limit concentration, the mixture will not be inflamed by a burner above water. If a point-like heating and ignition of the gas-mixture is carried out at the mixing-point under water, then the mixture is burning at the mixing-point only as long as the ignition-originator is present. Immediately after removing of the ignition-originator the flame will be disconnected by the water and extinguished.

It is possible acccording to this method to mix phosphine directly with air in the presence of water.

According to this invention, ordinary water and also water which contains anti-freezing-agents can be used in this device. Also thinned inorganic acids and thinned alkaline solutions or inorganic aqueous-solutions can be used.

This device is constructed in such a way that a quick thinning of the phosphine with air is effected under water with the consequence that the phosphine-air-mixture, which is leaving the water, is of a homogeneous nature. The most simple embodiment of this device, according to the invention, is consisting of a vertical pipe arranged to end under water, wherein the air is added through the pipe from below. This pipe has little openings in its wall through which the phosphine is flowing in, with the consequence that the mixture is always below the ignition limit concentration (=ignition limit).

The same effect can be achieved by using a water-jet-vacuum-pump whereby the phosphine is introduced into the water-jet and the air will be sucked in by the water-jet. A preferred embodiment of the device according to this invention can produce 100 $m_3$ phosphine thinned with air per hour.

Thereby the gas-mixture can contain up to 1,8% phosphine without any problems. In order to be able to mix phosphine with air without dangerous side-effects, it is advisable to flush all pipe-lines, in which phosphine will be transported, with $CO_2$, nitrogen or any other inert gas, before the beginning the process of phosphine generation. Then a fan or blower, which is transporting the air, will start to operate and come into function. It is further proposed to survey the air-stream in order to control any failure of air supply, since the air is necessary for thinning.

As soon as enough air and also enough water is present, the phosphine can be added. In case of any failure, like a blockage of the air-pipeline, a failure of the electric current or a surplus of phosphine, the addition of phosphine will be stopped automatically and all pipe lines will be flushed by an inert gas.

By this process, mixtures can be produced up to below the ignition limit. For normal gas treatments, such a high phosphine-content is not necessary, because much lower concentrations are sufficient. For the normal applications of the phosphine-air-mixture a phosphine-cocentration of 0,18% is used. In order to interrupt the working of the device, according to this invention, first the supply of phosphine will be stopped; then the pipe lines will be flushed by inert gas; then the fan will be stopped.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention.

DESCRIPTION OF INVENTION AND PREFERRED EMBODIMENT

Figure 1:
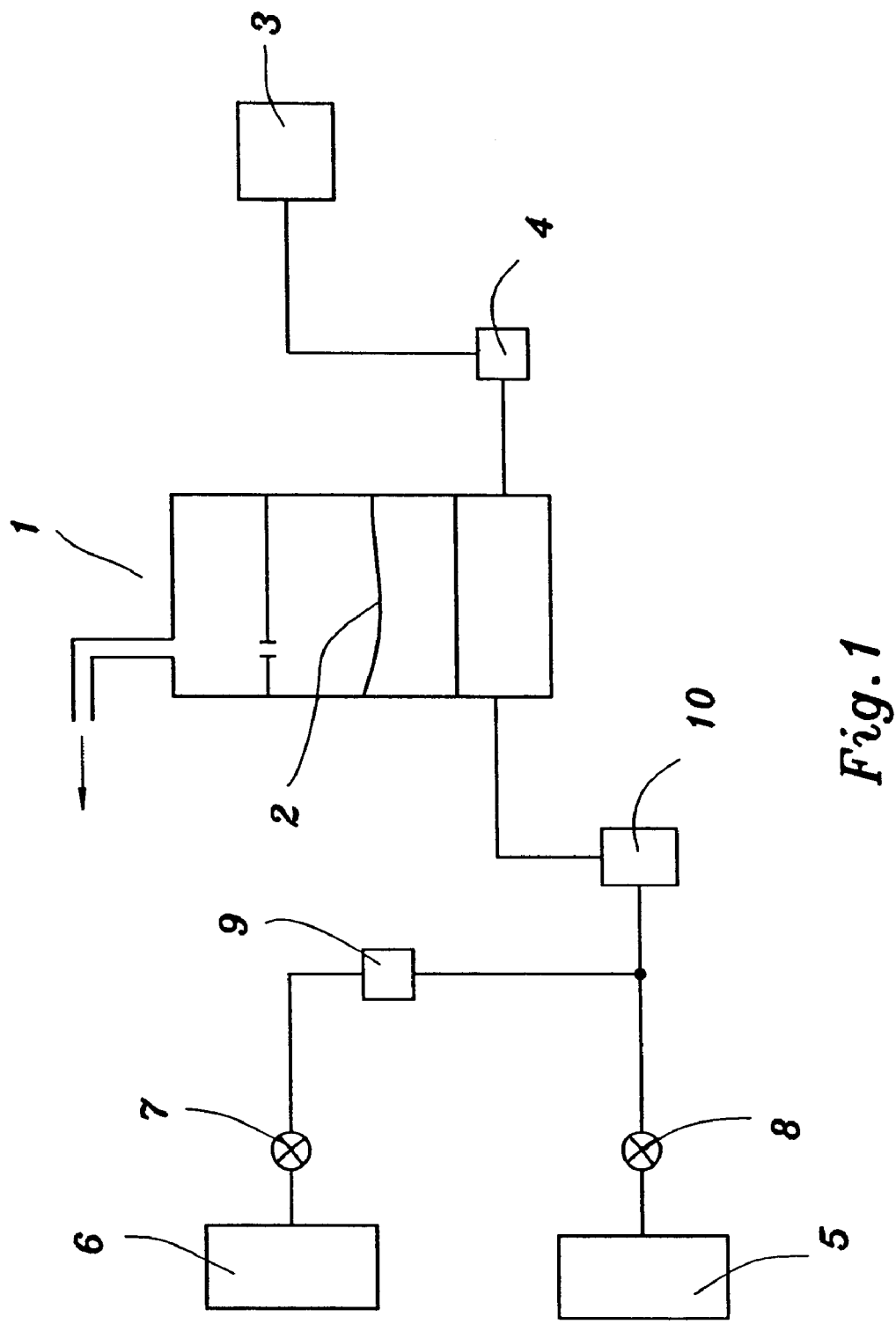
FIG. 1 is a schematic diagram illustrating a plant for phosphine generation.

In accordance with the present invention there is shown a flow-scheme concerning an embodiment of the process according to this invention is shown in the attached FIG. 1.

The element with the reference numeral 1 is a water-container; reference numeral 2 refers to the water-level; reference numeral 3 is the air-fan; reference numeral 4 is a flow-meter; reference numeral 5 is the phosphine-stock; reference numeral 6 is the stock of $CO_2$ and nitrogen; reference numerals 7 and 8 are valves, and reference numerals 9 and 10 represent flowmeters. Reference numeral 11 is the flow-out-opening at the upper edge of the water-container 1 with flow-out-pipe-line for the gas-mixture, which is the product of the process according to the present invention.

Figure 2:
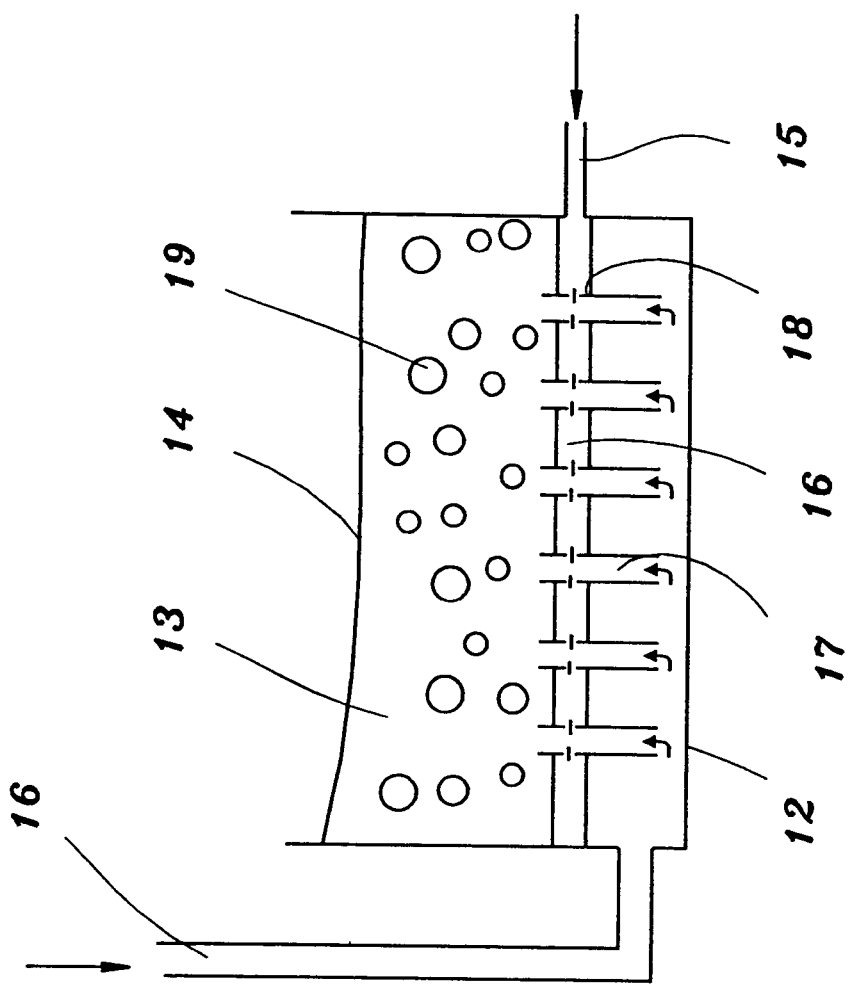
FIG. 2 is a schematic diagram illustrating a water container as a preferred embodiment of the present invention.

A preferred embodiment of the device according to this invention is described in FIG. 2. Reference numeral 12 shows the water container; reference numeral 13 the water content and the waterin the water container; reference numeral 14 designates the survey and the surface of the water; reference numeral 15 designates the phosphine-pipe-line, and reference numeral 16 designates the air-pipe-line. The phosphine-pipe-line is leading into the mixing-tube 16, which carries the air-pipes 17, which air pipe 17 carries phosphine-lead-in-openings 18.

All these pipelines or tubes are filled with water by the pressure of the water content and water mass 13. The mixing process of air and phosphine will take place as described above.

The produced gas-mixture-portions will leave the water container 12 as pearls and bubbles 19.

Figure 3:
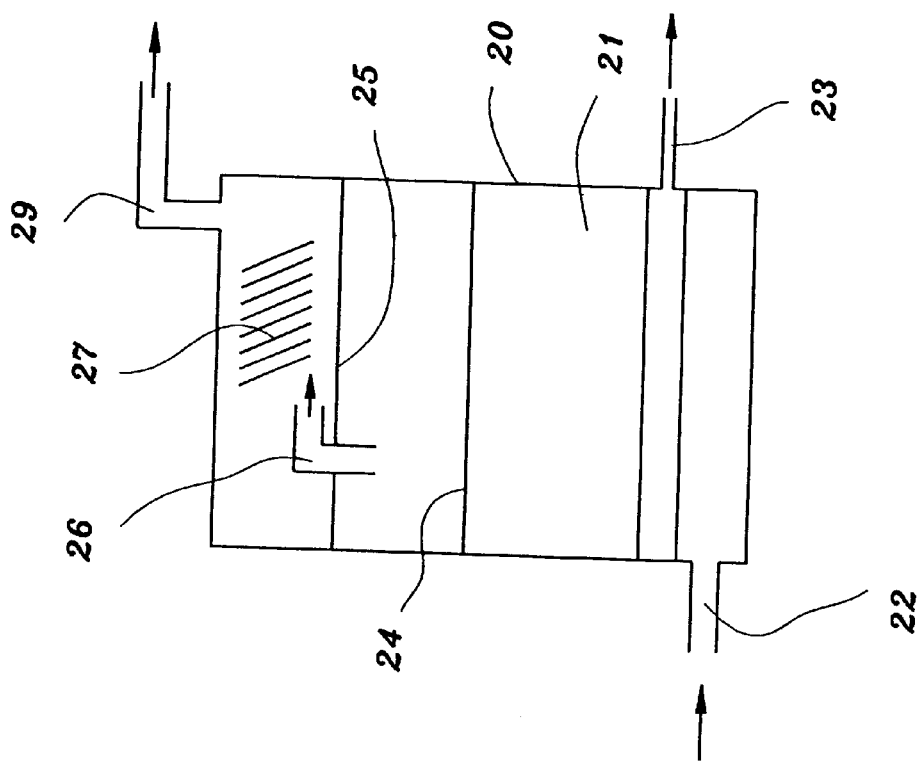
FIG. 3 is a schematic diagram illustrating a water container as another preferred embodiment of the present invention.

A further embodiment of the device according to this invention is shown in FIG. 3.

The water-container is associated with the reference numeral 20; reference numeral 21 is the water-content thereof; reference numeral 22 is the air-pipe-line; 23 is the phosphine-pipe-line. The water-surface has the reference numeral 24. A separating wall 25 is arranged in the upper part of the water-container, wherein the gas mixture air-phosphine will be gathered in the neighborhood of the upper part of the water-container, which gas mixture air-phosphine streams away through the opening 26. Reference numeral 27 is marking a dropping-separator arranged in room 28, from which the gas-mixture is streaming and flowing away through pipe-line 29.

Figure 4:
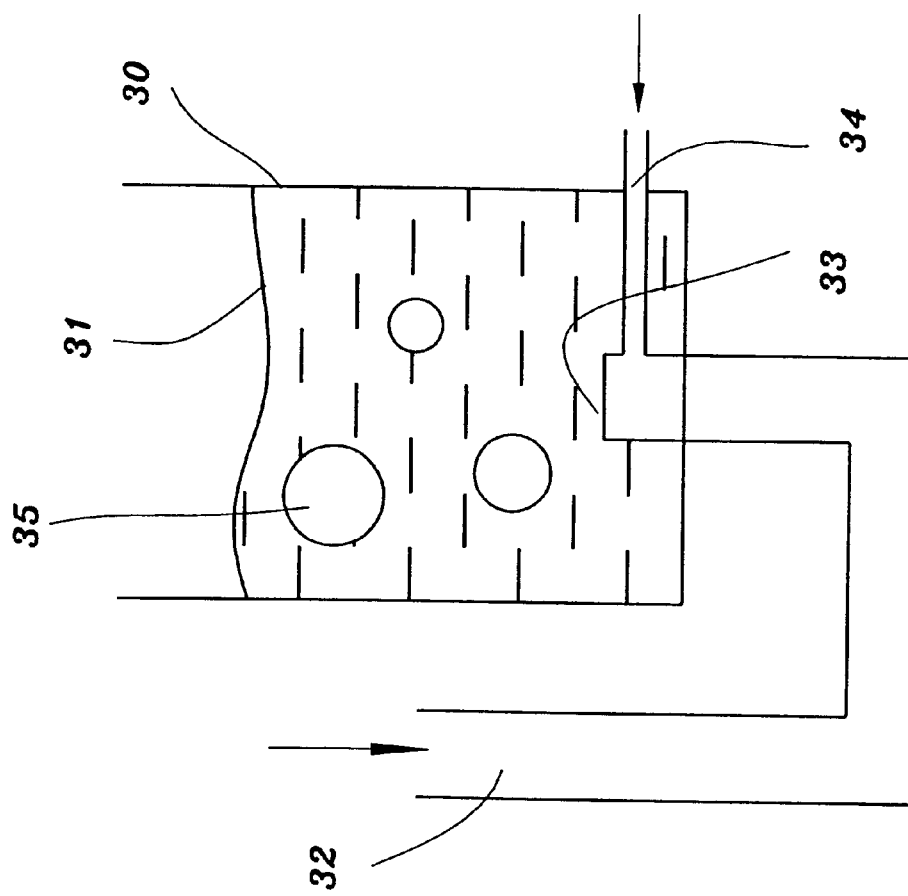
FIG. 4 is a schematic diagram illustrating a water container as yet another preferred embodiment of the present invention.

Another embodiment of the device according to this invention is described in FIG. 4.

Reference numeral 30 is the water container; reference numeral 31 is the water-surface. A pipe-line 32 for air is leading through the bottom of the water-container 30 into the inner room of the water container. This pipe-line 32 has connected immediately in front of its mouth 33 a sidewardly arranged supply-pipe-line 34 for phosphine. The mixing and whirling of air and phosphine take place mainly in the mouth-area 33 of the air-supply-pipe-line and an outlet is present following into the water volume of the water-container 30.

Preferably the delivery-pipe 32 has a diameter which is much larger than the diameter of the delivery-pipe 34 for the phosphine.

Due to the hydrostatic pressure of the water-column the water enters into the mouth-area of the air-delivery-pipe with the consequence that the process of this invention can be carried out in an optimal manner.

The upwardly streaming bubbles are designated with the reference numeral 35, which upwardly streaming bubbles consist of a mixture of air-phosphine.

The nature of this invention is described by the following examples.

EXAMPLE

A grain-silo of a noodle-factory, which has a height of 22 meters and a diameter of 18.5 meters, in which 5000 tons of grain are stored, has been treated by an air-phosphine-mixture, which has been produced according to this invention.

For this purpose 4900 grams of phosphine coming from a normal steel-cylinder have been thinned directly with air, using the device, which has been described in FIG. 3. A fan has been used, which is pumping 1400 $m_3$ per hour through the thinning device.

During the introduction of the gas into the silo, the silo is open above, in order to cause the gas-air-mixture to replace the air in the air space, wherein the air will escape at the top.

The first step of the process was to blow clean air from the device into the silo from below, in order to check that the pipe lines, which have a diameter of 20 cm, will have no higher hindrances or blockages in their path. Before the entrance into the grain, a superpressure of 3 cm water-column has been stated.

After having flushed the phosphine-pipe-lines by $CO_2$, coming from a second steel-cylinder, it was possible to lead phosphine from the thinning-device into the air-stream. In the first two minutes a flowmeter stated a flow-rate of 10 g per minute.

Than the flow-rate was increased to 50 g per minute.

After a further 5 minutes the phosphine-air-mixture stream has been stabilized at 80 g per minute.

After a time of one hour and 4 minutes in the upper free-room of the grain-silo a concentration of 50 ppm phosphine was measured. The air-phosphine-mixture has removed the air which was placed in the interspaces between the grain-particles.

This removed air migrated like in an chromatographic colum, upwards.

Than the supply of phosphine was stopped and the phosphine-pipeline was flushed by $CO_2$. After an additional minute also the blower was stopped and the silo was tightly closed at the bottom below and and at the top above in order to cause the gas to be effective.

During delivery of phiosphine gas, the phoshine concentration was measured in the gas-air leading pipe-lines.

After 3 minutes of inflow time, 1600 ppm phosphine could be measured by a Dräger-tester.

After 10 minutes the gas-concentration had been stabilized at 2300 ppm phosphine. This concentration was measured also shortly before the process had been stopped.

After the gas-treatment, a concentration of 2200 ppm of phosphine was measured at the bottom of the grain.

24 hours after the gas-treatment the following results of measurements were present in the grain:

Upper part of the silo, 1 m below the grain-surface: 1200 ppm phosphine.

Under part of the silo, 1 m above the bottom: 800 ppm phosphine.

It will be understood that each of the elements described above, or two or more together, may also find a useful application in other types of phosphine mixing system configurations and phosphine gas processing procedures differing from the types described above.

While the invention has been illustrated and described as embodied in the context of mixing phosphine with air, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A process for the direct thinning of phosphine with air up to a phosphine-concentration of 1.8% maximum wherein the mixing of the gases is carried out under water.

2. The process according to claim 1, wherein the water is containing anti-freezing-agents and/or anti-corrosion-agents and/or anti-flame-agents.

3. The process according to claim 2, wherein water is pumped through a device and phosphine is added to the water.

4. The process according to claim 1, wherein phosphine is added laterally through openings which are arranged in a pipe which is standing in water and in which piped-air is introduced.

5. The process according to claims 1, wherein the gas-mixture is leaving the device through a dropping-separator for preventing that water is coming to the gas-pipe-lines.

6. The process according to claims 1, wherein the process is controlled by an electronic circuit.

7. The process according to claims 1, wherein the water contains free hydrogen-ions wherein the water reacts like an acid.

8. The process according to claims 1, wherein the water contains free hydroxyl-ions, wherein the water has the character of a leach.

9. The process according to claims 1, wherein the water contains metallic cations and non-metallic anions wherein the water reacts like an electrolyte.

10. A method for the direct thinning of phosphine with air comprising feeding air to be in a presence of water;

feeding phosphine to be in the presence of water;

mixing the air and the phosphine under water up to a phosphine-concentration of 1.8% mole percent phosphine of the mixed gas.

11. The method according to claim 10 further comprising feeding air to be under water;

feeding phosphine to be under water;

mixing the air and the phosphine under water up to a phosphine-concentration of 1.8% mole percent phosphine of the mixed gas.

12. The method according to claim 10 further comprising adding a member selected from the group consisting of an anti-freezing-agent, an anti-corrosion-agent, an anti-flame-agent and mixtures thereof to the water;

pumping water through the device and addding phosphine to the water.

13. The method according to claim 10 further comprising adding phosphine laterally through openings which are arranged in a pipe which is standing in water and wherein piped-air is introduced into the pipe;

the gas-mixture leaving the device through a dropping-separator in order to prevent that water is coming to the gas-pipe-lines;

controlling the method with an electronic circuit.

14. The method according to claim 10, wherein the water contains free hydrogen-ions and wherein the water reacts like an acid.

15. The method according to claim 10, wherein the water contains free hydroxyl-ions, wherein the water reacts like a base.

16. The method according to claim 10, wherein the water contains metallic cations and non-metallic anions wherein the water contains a salt-portion.

* * * * *